United States Patent [19]

Born

[11] 4,046,140
[45] Sept. 6, 1977

[54] CERVIX PHOTOGRAPHIC METHOD

[76] Inventor: Grant R. Born, 5180 Kalamazoo, SE., Grand Rapids, Mich. 49508

[21] Appl. No.: 639,854

[22] Filed: Dec. 11, 1975

Related U.S. Application Data

[62] Division of Ser. No. 259,088, June 2, 1972, abandoned.

[51] Int. Cl.² .................................................. A61B 1/00
[52] U.S. Cl. ....................................................... 128/2 R
[58] Field of Search ................ 128/2 R, 2 B, 2 A, 3, 128/6, 22, 344, 398, 408; 354/62, 63, 159, 127, 128, 139, 145, 149

[56] References Cited

U.S. PATENT DOCUMENTS

| 1,246,340 | 11/1917 | Smit | 128/6 |
| 1,616,722 | 2/1927 | Vernon | 128/3 |
| 2,746,450 | 5/1956 | Lady et al. | 128/6 |
| 3,096,764 | 7/1963 | Uddenberg | 128/2 A |
| 3,195,431 | 7/1965 | Augustin, Jr. et al. | 354/62 |
| 3,330,193 | 7/1967 | Kaess | 354/145 |
| 3,638,643 | 2/1972 | Hotchkiss | 128/22 |

OTHER PUBLICATIONS

Bushnell, "Obstetrics & Gynecology," vol. 22, No. 2, Aug. 1963, pp. 190-198.

*Primary Examiner*—William E. Kamm
*Attorney, Agent, or Firm*—Price, Heneveld, Huizenga & Cooper

[57] ABSTRACT

An apparatus and method for photographing the cervix for diagnostic and treatment purposes includes a speculum and a special close-up camera having a ring-shaped flash lamp surrounding its lens aperture. The outer diameter of the speculum is sufficiently large to dilate the vaginal opening and the inner diameter is adapted to surround the cervix. The innermost end of the speculum is beveled for ease of insertion and for positioning over the cervix while the opposite end is adapted for positioning adjacent the flash lamp and lens of the camera. In use, the walls of the speculum act as a fiber-optic system illuminating the cervix. The resulting photograph is actual size such that lesions and other abnormalities may be accurately measured directly on the print.

3 Claims, 4 Drawing Figures

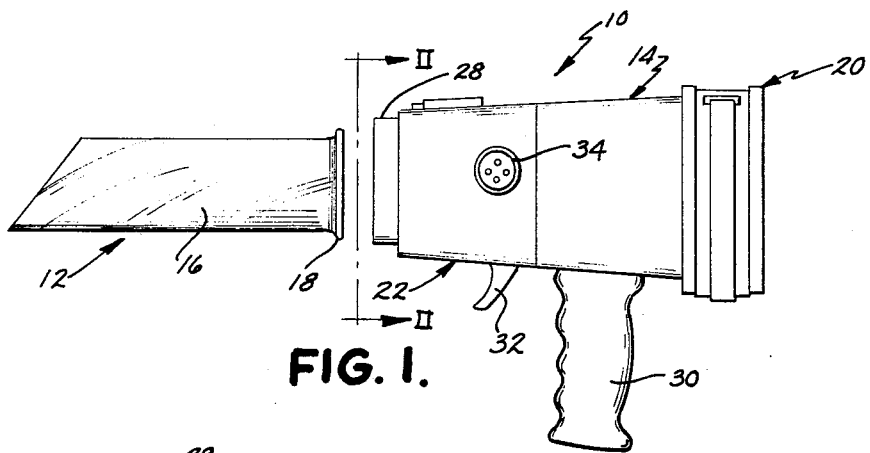
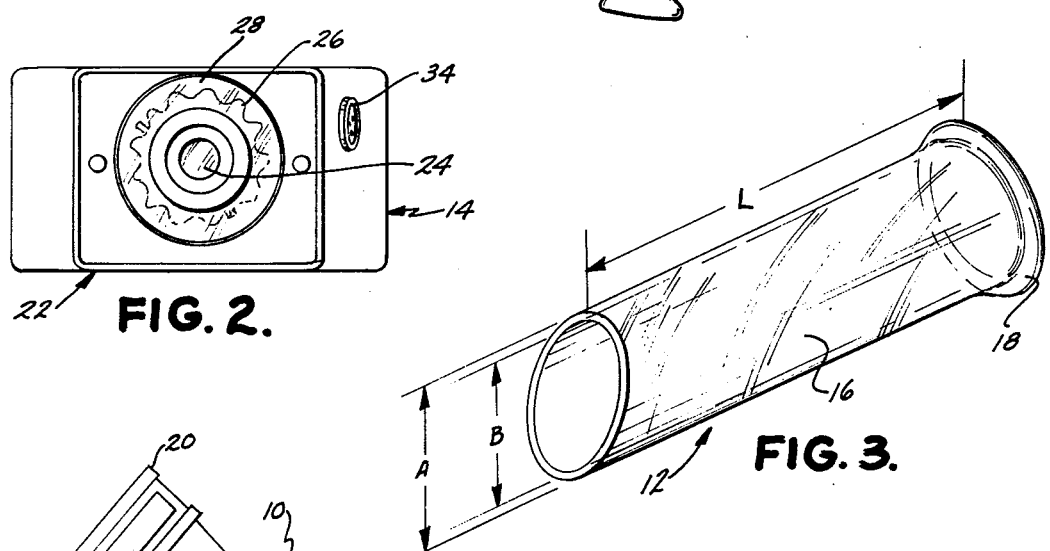
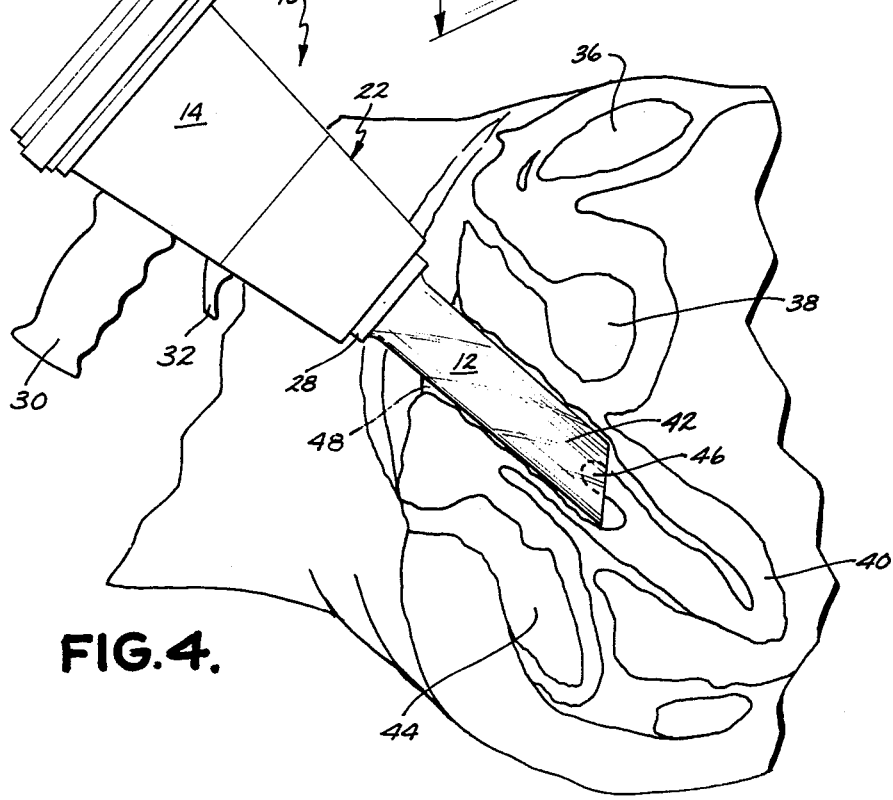

CERVIX PHOTOGRAPHIC METHOD

CROSS REFERRENCE TO RELATED APPLICATION

This is a division of application Ser. No. 259,088, filed June 2, 1972 now abandoned.

BACKGROUND OF THE INVENTION

This invention relates to a method for photographing the female cervix for diagnostic and treatment purposes. Prior art devices for this purpose utilize complex specialized equipment and must generally be operated by one specially trained in photographic techniques. In addition to the elaborate photographic equipment required, cervical photography utilizing the present day equipment results in a photograph illustrating not only the cervix, but other parts of the genital area including pubic hair, the vaginal wall, etc., rendering interpretation of the photographs difficult. Because of variations in the object and image distances, the resulting photographs are not consistent and are of an enlarged or reduced size. Measurements of lesions or other abnormalities taken from these photographs thus, are not accurately representative. Subsequent photographs taken to follow the progress of treatment cannot accurately be compared to the first photograph to determine effectiveness of treatment and the like.

SUMMARY OF THE INVENTION

The present invention overcomes the objections of prior art cervical photography apparatus; provides relatively instant results; requires only a minimum of apparatus which the non-photographer doctor can operate easily; and provides a well-focused correctly exposed photograph each and every time it is operated. The features are provided in the present invention by the combination of a special close-up camera having a ring-like flash lamp surrounding the lens and a speculum having a predetermined length match to the focal length of the camera thereby eliminating the need for exposure and focusing computations. The resulting photograph illustrates only the cervix and provides an accurate subject-image ratio which may be accurately measured and compared with subsequent photographs to follow the progress of a given medical treatment.

Accordingly, it is an object of the present invention to provide a method of photographing specific parts of the female genital area simply, rapidly, and with great accuracy.

Another object of the present invention provides a new and improved method for internal photography of the vagina.

It is yet another object of the invention to provide a photographic method for photographing the cervix without illustrating other parts of the genital area.

Yet another object of the present invention provides a cervical photographic method wherein the camera may be accurately positioned with respect to the cervix to provide an accurate, perfectly focused photograph.

It is yet another object of the present invention to provide a cervical photographic method which is extremely simple and may be performed by one having no special photographic training.

These and other important objects and advantages of the present invention will become readily apparent to those skilled in the art upon reading the following description with reference to the accompanying drawings illustrating a preferred embodiment of the invention.

BRIEF DESCRIPTION OF THE DRAWINGS

FIG. 1 is a plan view of a speculum and camera utilized in the present invention;

FIG. 2 is a view taken along the plane II—II of FIG. 1 illustrating the front or lens portion of the camera;

FIG. 3 is a perspective view of the speculum shown in FIG. 1; and

FIG. 4 is a simplified anatomical illustration showing the invention in use.

DESCRIPTION OF THE PREFERRED EMBODIMENT

Referring now to the drawings, and in particular to FIG. 1, the apparatus of the invention will be described in greater detail. Basically, the invention illustrated generally by the numeral 10 includes a hollow, elongated tubular speculum 12 and a camera 14. As best illustrated in FIG. 3, the speculum is an elongated tube which is similar to the conventional tubular speculum used for vaginal medical examinations and commonly referred to as a Ferguson speculum. The speculum is constructed of a glass-like material such as Pyrex which is easily cleaned and sterilized.

A central elongated tubular portion 16 of the speculum has an outer diameter indicated by the dimension A sufficiently large to dilate the vagina. The inner diameter indicated at B is large enough to surround the cervix in a manner which will hereinafter be described. The leading or insertion end of the speculum is beveled such that it is inclined at an angle preferably of 30° to 45° with respect to its elongated axis. The opposite or external end flares annularly outwardly to form a flange or annular lip 18. The length of the tube indicated at L is somewhat longer than the length of the vagina from the vaginal orifice to the cervix.

In the preferred embodiment, the length of the speculum from the outwardly extending flange to the apex of the bevel is 14 centimeters (cm) and the opposite side (i.e., at the inwardly tapering portion of the bevel to the annular flange) is 12 centimeters. The inside diameter is 4 cm and the wall thickness is approximately 2 millimeters (mm). The annular flange at the outmost end forms a wall of approximately 4 mm. While the preferred embodiment is formed of glass, other transparent plastic-like materials may be used with equal facility.

The short range camera 14 (FIGS. 1, 2, and 4) is preferably of the well-known self-processing type which produces a finished black and white print in a matter of a few seconds and in approximately one minute for color prints. One such camera suitable for use in this invention is known as the "Polaroid CU-5 Close-Up Camera," a fixed focus camera with built-in flash unit. This type of camera is commonly used for industrial photography and is commercially available from the Polaroid Corporation, 730 Main Street, Cambridge, Massachusetts 02139, and is described in detail in U.S. Pat. No. 3,330,193 issued July 11, 1967, and assigned to the Polaroid Corporation.

Camera 14 includes two sections—a rear or film pack section 20 and a front or lens section 22 which houses the lens and shutter mechanisms 24 (FIG. 2). A ring-like flash lamp 26 is positioned in an annular housing 28 fixed on the front section and surrounds the lens and shutter assembly 24. A reflector positioned behind the flash lamp in the annular housing serves to direct the light outwardly therefrom. A handle or piston grip 30 depends downwardly from the rear section of the housing for ease in handling and convenient operation of a shutter release trigger 32. A plug 34, electrically connected to the flash lamp and shutter assembly is provided for electrical connection to a suitable power supply (not shown) for energizing the flash lamp when the camera is operated and the shutter opened.

This particular type of camera is available with a wide range of accessories including various lens assemblies and ratio mulitpliers which may be conveniently attached to provide enlarged or reduced size photos. In the preferred embodiment, however, a lens of 75 mm (3 inch) focal length is used to provide, when used with the previously described speculum, a 1:1 or full-size subject-image ratio. For a complete and detailed mechanical description and operation of the camera assembly, reference may be had to U.S. Pat. No. 3,330,193.

Referring to FIG. 4, the apparatus of the present invention is shown in use by means of a simplified anatomical illustration. The basic portions of the anatomy illustrated include the symphysis 36, the bladder 38, the uterus 40, the vagina 42, and the rectum 44. The narrow outer end of the uterus, the cervix, is illustrated at 46 and the vaginal opening is illustrated by the numeral 48.

In use, the speculum 12 is suitably lubricated and the beveled end portion aids in the insertion thereof. The speculum is inserted into the vaginal opening 48 in a coventional manner with slight gentle rotational motion and is urged inwardly along the length of the vagina 42 until the cervix 46 is positioned in the inner diameter at the beveled end. Camera assembly 14 is then positioned adjacent the outer end 18 of the speculum such that the flash lamp 26 and housing 28 surrounding the flash lamp abuts the flange 18 on the speculum. In this position, the camera lens is positioned at the correct distance for the cervix to be photographed. No focusing is required.

The camera, in this position, is operated in a conventional manner by squeezing the release trigger 32 causing the shutter to open simultaneously with operation of the flash lamp 26. The side walls of the speculum are transparent and operate in the manner of a fiber-optic system to transmit and concentrate the light from the flash lamp at the area immediately surrounding the cervix. After the exposure is made, the camera is removed from its abutting relationship with the flanged end of the speculum and the exposed film is developed in the particular manner characteristic of the above-described camera. The resulting photograph is properly focused and illustrates the cervix in extremely clear detail.

It will be appreciated readily by those skilled in the art that the photo resulting from the described procedure may be used for diagnosis, treatment, comparison with subsequent or previous photos to monitor the progress of treatment and the like. The photos are accurate and may be used for accurate measurements of lesions and other abnormalities. In addition, the resulting photograph is not objectionable to the female patient since no objectional areas are illustrated. Only the cervix is illustrated and the patient does not object to subsequent photographs since she can see and watch the progress of treatment. Since the apparatus operates so simply, special photographic training is not required. Accordingly, the non-photographer doctor can simply and accurately provide the required photographs with excellent results.

While a preferred embodiment of this invention has been illustrated and described in detail, it will be recognized that other modifications incorporating the teachings hereof can readily be made in the light of this disclosure. For example, lenses having greater or lesser focal lengths, ratio multipliers, and like accessories may be utilized to provide photographs having larger or smaller subject-to-image ratios. If desired, the length of the speculum may also be varied to provide different subject-image ratios and the resulting enlarged or reduced sized photographs. It is important to note that subsequent photos should be taken with a speculum having the same length relationship to that of the focal length of the camera so that accurate comparisons can be made.

Light filters or specialized film may also be utilized with this invention as, for example, a suitable infrared film to detect and illustrate the vascular supply to the cervix area. Pictures of this type can be utilized, typically, for early cancer detection and the like.

While a special type of camera having a built-in flash lamp has been described, other types of cameras and sources of illumination may also be utilized. Similarly, the tubular speculum need not include the annular flange at its ends. Accordingly, all modifications embodying the principles of this invention are to be considered as included in the following claims unless these claims by their language expressly state otherwise.

The embodiments of the invention in which an exclusive property or privilege is claimed are defined as follows.

1. The method of photographing the cervix and using the photos so obtained for diagnostic and treatment purposes comprising the steps of:

providing an elongated, hollow, open-ended tubular member having a preselected length formed from transparent material;

inserting the member through the vaginal opening thereby dialating the walls thereof;

continuing the inserting step until the inner open end of the member surrounds the cervix;

providing a close-up, fixed focus camera having an annular flashlamp surrounding its lens, the diameter of said lamp being substantially equal to the diameter of said member, the focus of said camera being such as to produce a predetermined and subsequently reproducible subject-image ratio enabling photos taken through utilization of this, the preceding and following steps to be used for accurate and comparative measurements of lesions and other abnormalities throughout the course of treatment of a particular patient;

positioning said camera so that said flashlamp is in abutment and axially aligned with the exposed end of said member;

triggering said camera to cause its lens to open and its flashlamp to momentarily illuminate;

transmitting the illumination from said flashlamp along the sidewalls of said member and thereby concentrating the light from the flashlamp at the area immediately surrounding the cervix to expose the film;

removing the camera from abutment with the member removing the member and developing the film so exposed; and using the photo so obtained for diagnostic and treatment purposes.

2. The method as set forth in claim 1 which further comprises the step of preselecting the length of said member to provide a 1:1 subject-image ratio.

3. The method as set forth in claim 1 further comprising the steps of:
   producing a second photo of the cervix in accordance with the steps of claim 14 after a predetermined time; and
   comparing the second photo to the earlier photo to thereby detect changes in the appearance of the cervix.

* * * * *